(12) United States Patent
Dubois et al.

(10) Patent No.: US 10,117,747 B2
(45) Date of Patent: Nov. 6, 2018

(54) PROSTHESIS

(71) Applicants: OBL SA, Chatillon (FR); Centre Hospitalier Universitaire de Dijon, Dijon (FR)

(72) Inventors: Guillaume Dubois, Chatillon (FR); Narcisse Zwetyenga, Dijon (FR)

(73) Assignees: OBL SA, Chatillon (FR); Centre Hospitalier Universitaire de Dijon, Dijon (FR)

( * ) Notice: Subject to any disclaimer, the term of this patent is extended or adjusted under 35 U.S.C. 154(b) by 131 days.

(21) Appl. No.: 14/959,464

(22) Filed: Dec. 4, 2015

(65) Prior Publication Data
US 2016/0081806 A1    Mar. 24, 2016

Related U.S. Application Data

(63) Continuation of application No. PCT/EP2014/061687, filed on Jun. 5, 2014.

(30) Foreign Application Priority Data

Jun. 7, 2013    (EP) .................................... 13305770

(51) Int. Cl.
*A61F 2/30*    (2006.01)
*A61F 2/46*    (2006.01)

(52) U.S. Cl.
CPC .......... *A61F 2/3099* (2013.01); *A61F 2/4603* (2013.01); *A61F 2/30942* (2013.01); *A61F 2002/304* (2013.01); *A61F 2002/30387* (2013.01); *A61F 2002/30398* (2013.01); *A61F 2002/30578* (2013.01);

(Continued)

(58) Field of Classification Search
CPC .............................. A61F 2/3009; A61F 2/0059
See application file for complete search history.

(56) References Cited

U.S. PATENT DOCUMENTS 6,132,466 A    10/2000  Hoffman et al.
2009/0112331 A1*  4/2009  Hunter .................. A61L 27/306
                                                 623/23.53

(Continued)

FOREIGN PATENT DOCUMENTS

EP    0628293 A1   12/1994
FR    2558721 A1    8/1985

OTHER PUBLICATIONS

International Search Report and Written Opinion dated Oct. 17, 2014 issued on related Application PCT/EP2014/061687, filed Jun. 5, 2014, 14 pages.

*Primary Examiner* — Jason-Dennis Stewart
(74) *Attorney, Agent, or Firm* — EIP US LLP (57) ABSTRACT

A temporo-mandibular joint prosthesis comprising: a first part for attaching to a temporal bone; a second part for attaching to a mandible bone; and a mechanism linking the first part and the second part. The mechanism defines a range of motion of the first part relative to the second part for when the first and second parts are attached to a temporal bone and a mandible bone, respectively. The mechanism includes a rotary joint providing a rotational range of motion of the first part relative to the second part; and a first slider joint providing a first translational range of motion of the first part relative to the second part.

15 Claims, 8 Drawing Sheets (52) U.S. Cl.
CPC .............. *A61F 2002/30649* (2013.01); *A61F 2002/30991* (2013.01); *A61F 2002/30993* (2013.01)

(56) References Cited

U.S. PATENT DOCUMENTS

| | | |
|---|---|---|
| 2009/0138092 A1 | 5/2009 | Johnston et al. |
| 2013/0331944 A1* | 12/2013 | Touleimat ............. A61F 2/3099 623/17.17 |

* cited by examiner

PROSTHESIS

CROSS-REFERENCE TO RELATED APPLICATIONS

This application is a continuation under 35 U.S.C. § 120 of International Application No. PCT/EP2014/061687, filed Jun. 5, 2014, which claims priority to EP Application No. 13305770.3, filed Jun. 7, 2013. The entire contents of the above-referenced patent applications are hereby incorporated by reference.

BACKGROUND OF THE INVENTION

Field of the Invention

The present invention relates to a prosthesis, particularly a temporo-mandibular joint prosthesis.

Description of the Related Technology

The temporo-mandibular joint in a human body joins the temporal bone of the skull with the mandible bone. The mandible bone may be referred to as the lower jaw bone, which meets the maxilla bone, i.e. the upper jaw, when the jaws are closed. More specifically, in the temporo-mandibular joint, the condyle part of the mandible interfaces with the fossa part of the temporal bone, via an articular disc of fibrocartilagenous tissue.

The temporo-mandibular joint determines movement of the upper and lower jaws, by movement of the mandible bone relative to the temporal bone.

Prostheses for replacing part or all of a temporo-mandibular joint are known. However, it is not straightforward to devise a prosthesis which offers the same or similar functionality as the natural temporo-mandibular joint, so as to provide a joint which for example offers the complex range of motion of the natural joint, an acceptably low risk of dislocation, and a compact joint size.

Known temporo-mandibular joint prostheses use a ball and socket type joint to provide the range of motion; however, this offers a more limited range of motion compared with the natural temporo-mandibular joint.

One known temporo-mandibular joint prosthesis has one joint with a condylar head interfacing with a bearing surface. The form of the bearing surface permits rotational and a translational movement of the condylar head relative to the bearing surface; however, this configuration brings a greater risk of dislocation of the joint.

SUMMARY

According to first embodiments, there is provided a temporo-mandibular joint prosthesis comprising:
 a) a first part for attaching to a temporal bone;
 b) a second part for attaching to a mandible bone; and
 c) a mechanism linking the first part and the second part, the mechanism defining a range of motion of the first part relative to the second part for when the first and second parts are attached to a temporal bone and a mandible bone, respectively,
the mechanism including:
 a rotary joint providing a rotational range of motion of the first part relative to the second part; and
 a first slider joint providing a first translational range of motion of the first part relative to the second part.

In accordance with further embodiments, there is provided a rotary joint for providing a rotational range of motion of a first part of a temporo-mandibular joint prosthesis relative to a second part of the temporo-mandibular joint prosthesis, the temporo-mandibular joint prosthesis comprising:
 a) the first part for attaching to a temporal bone;
 b) the second part for attaching to a mandible bone; and
 c) a mechanism linking the first part and the second part, the mechanism defining a range of motion of the first part relative to the second part for when the first and second parts are attached to a temporal bone and a mandible bone, respectively, the mechanism including:
  the rotary joint; and
  a first slider joint providing a first translational range of motion of the first part relative to the second part.

According to other embodiments, there is provided a part for a temporo-mandibular joint prosthesis, wherein the part is configured for attaching to one of a temporal bone and a mandible bone, and for linking by a mechanism of the temporo-mandibular joint prosthesis to another part for attaching to the other one of a temporal bone and a mandible bone, the mechanism defining a range of motion of the parts relative to each other for when each of the parts is attached to different of a temporal bone and a mandible bone, the mechanism including:
 a rotary joint providing a rotational range of motion of the parts relative to each other; and a first slider joint providing a first translational range of motion of the parts relative to each other.

In other embodiments, there is provided a method of implanting in a patient a temporo-mandibular joint prosthesis, the temporo-mandibular joint prosthesis comprising:
 a) a first part for attaching to a temporal bone;
 b) a second part for attaching to a mandible bone; and
 c) a mechanism linking the first part and the second part, the mechanism defining a range of motion of the first part relative to the second part for when the first and second parts are attached to a temporal bone and a mandible bone, respectively, the mechanism including:
 a rotary joint providing a rotational range of motion of the first part relative to the second part; and
 a first slider joint providing a first translational range of motion of the first part relative to the second part, the method including:
 i) attaching the first part to a temporal bone of the patient; and
 ii) attaching the second part to a mandible bone of the patient.

Further features will become apparent from the following description of embodiments, given by way of e ample only, which is made with reference to the accompanying drawings.

DETAILED DESCRIPTION OF CERTAIN INVENTIVE EMBODIMENTS

In embodiments described herein, there is provided a temporo-mandibular joint prosthesis comprising:
 a) a first part for attaching to a temporal bone;
 b) a second part for attaching to a mandible bone; and
 c) a mechanism linking the first part and the second part, the mechanism defining a range of motion of the first part relative to the second part for when the first and second parts are attached to a temporal bone and a mandible bone, respectively, the mechanism including:
  a rotary joint providing a rotational range of motion of the first part relative to the second part; and
  a first slider joint providing a first translational range of motion of the first part relative to the second part.

An example of such a temporo-mandibular joint prosthesis embodiment will now be described with reference to FIGS. 1 and 2.

Figure 1:
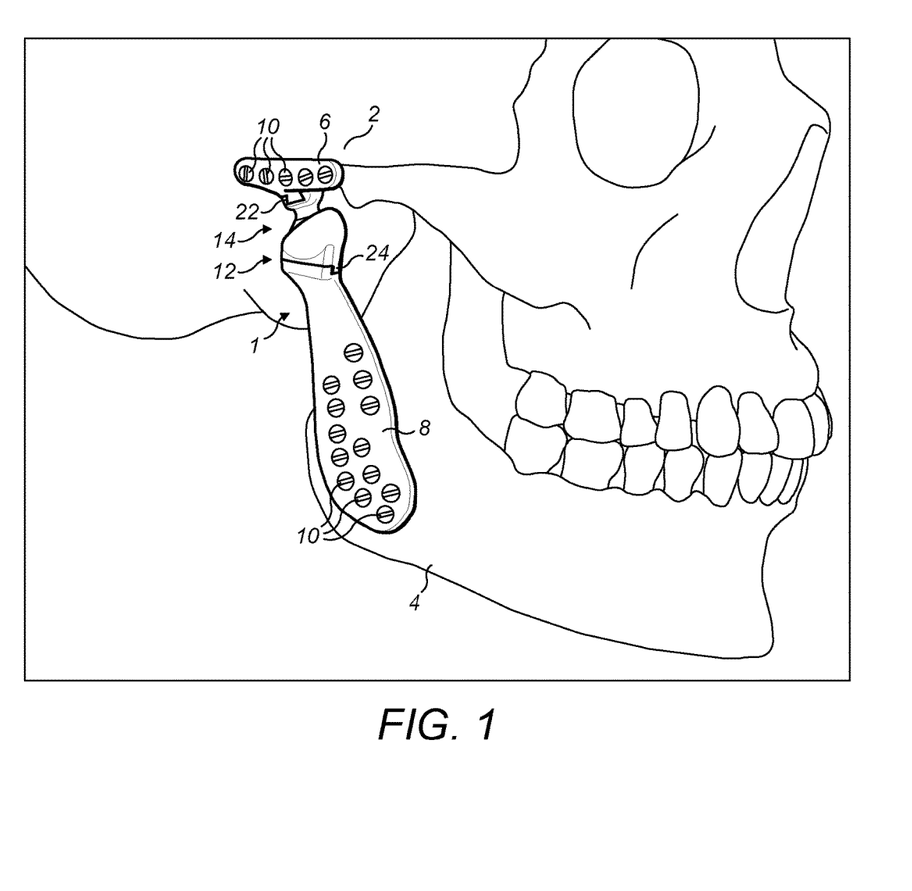
FIG. 1 shows schematically an embodiment of a temporo-mandibular joint prosthesis.
Figure 2:
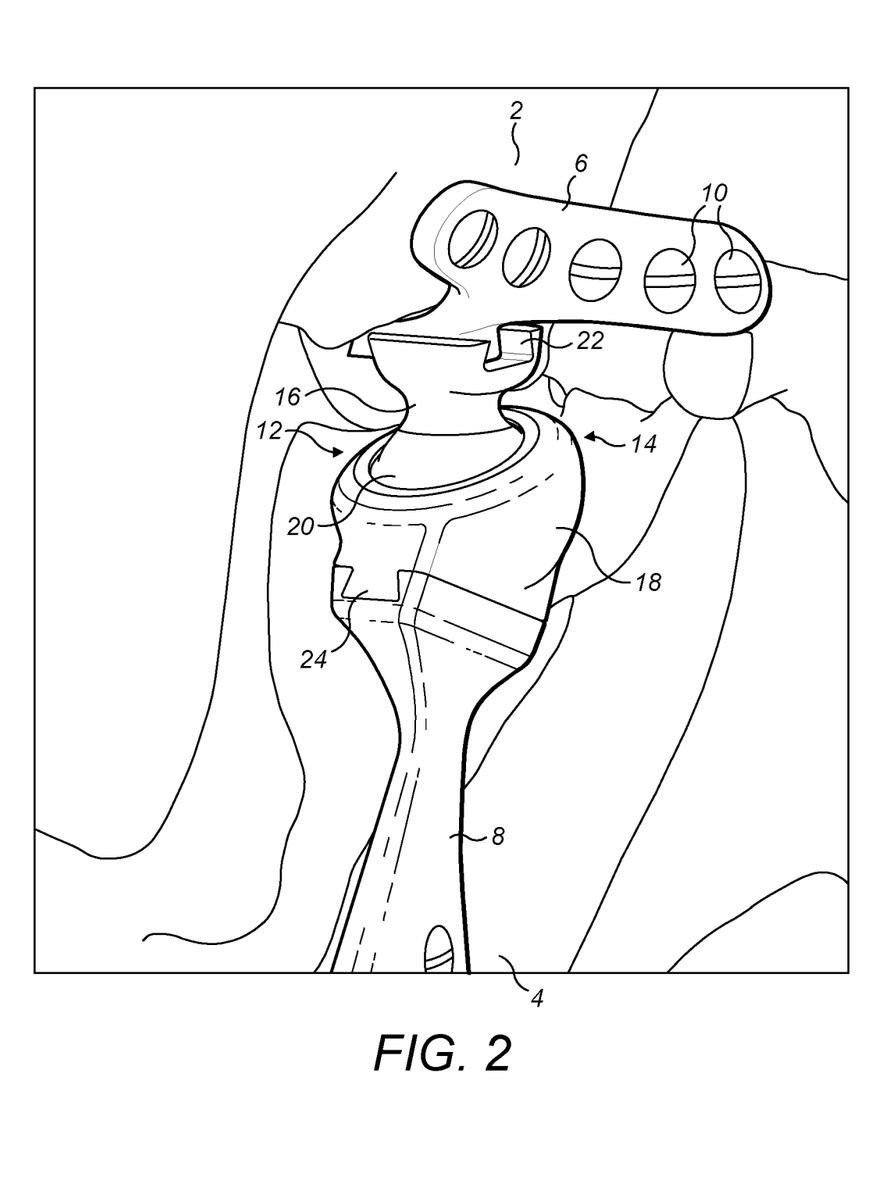
FIG. 2 shows schematically a different view of the embodiment.

FIGS. 1 and 2 show the example temporo-mandibular joint prosthesis 1 when attached to a human temporal bone 2 and mandible bone 4. The prosthesis 1 comprises a first part 6 attached to the temporal bone and a second part 8 attached to the mandible bone. Each of the first and second parts 6, 8 in this example comprises a plurality of holes, for attaching to the temporal and mandible bones, respectively, by osteosynthesis screws 10. The skilled person would understand that alternative techniques may be used to attach the parts to the bones.

Each of the first and second parts may be custom made in accordance with the anatomy of a patient, to ensure an accurate fit to the temporal and mandible bones the prosthesis is to fit to, so the prosthesis can operate correctly when implanted.

The first part 6 and the second part 8 are linked by a mechanism 12 which defines a range of motion of the first part relative to the second part, for when the first and second parts are attached to the temporal and mandible bones, respectively. In other words, the mechanism defines the range of motion for the temporo-mandibular joint prosthesis when implanted.

The mechanism 12 comprises a rotary joint 14 which provides a rotational range of motion of the first part relative to the second part. In this example, the rotary joint comprises a first element 16 and a second element 18. A surface of the first element rotatably interfaces with a surface of the second element. In this example, the rotary joint is a ball and socket joint; a portion of the first element has a convex surface 20 to form the ball part of the joint, and a portion of the second element has a concave surface (not shown) to form the socket part of the joint, which concave surface rotatably interfaces with the convex surface.

The mechanism 12 further comprises a first slider joint 22 which provides a first translational range of motion of the first part relative to the second part. In this example, the first slider joint 22 links the first part 6 to the first element 16. The first part is formed to slidably interface with the first element. The first slider joint 22 in this example is a dovetail slider joint. Therefore, as illustrated, a portion of the first part is formed as a longitudinal protrusion with a wedge shaped cross section, and a portion of the first element is formed as a channel with a wedge shaped cross section for receiving the protrusion; this configuration contributes to a mechanically stable and compact design of the prosthesis. In other examples, a portion of the first part may instead form the wedge shaped channel and a portion of the first element may instead form the wedge shaped protrusion received by the channel; this configuration also contributes to a mechanically stable and compact design of the prosthesis, but less so compared with the configuration of FIG. 1, although there may be other design reasons to use this configuration, for example to better accommodate the specific anatomy of a patient.

In this example, the mechanism 12 further comprises a second slider joint 24 which provides a second translational range of motion of the first part relative to the second part. In this example, the second slider joint 24 links the second part 8 to the second element 18. The second part is formed to slidably interface with the second element. The second slider joint 24 in this example is a dovetail slider joint. Therefore, similar as described for the first slider joint, a portion of one of the second part and the second element may be formed as a longitudinal protrusion with a wedge shaped cross section, and a portion of the other one of the second part and second element may be formed as a channel with a wedge shaped cross section for receiving the protrusion. Although both these second slider joint configurations provide a mechanically stable and compact design, it has been found that with a portion of the second element formed as the protrusion and a portion of the second part formed as a channel, a more mechanically stable and compact design of the prosthesis may be provided, although there may be other design reasons to use the other second slider configuration, for example to better accommodate the specific anatomy of a patient.

In this example, components of the sliding joints are integrally formed with the first and second parts, and the first and second elements of the rotary joint, by forming a portion of the first part and a portion of the first element to form the first sliding joint, and by forming a portion of the second part and a portion of the second element to form the second sliding joint. Thus, in combination with compactly designed rotary joint elements, a compact mechanism 12 may be realized having a wide range of motion both rotationally and translationally. Compared with a known prosthesis, embodiments described herein use separate joints to provide different of a rotational and translational range of motion, whilst still providing a compact prosthesis. Each joint may be designed specifically for one range of motion direction, with any desired limits of that range of motion, rather than comprising the functionality by combining the different ranges of motion in one joint.

Figure 3:
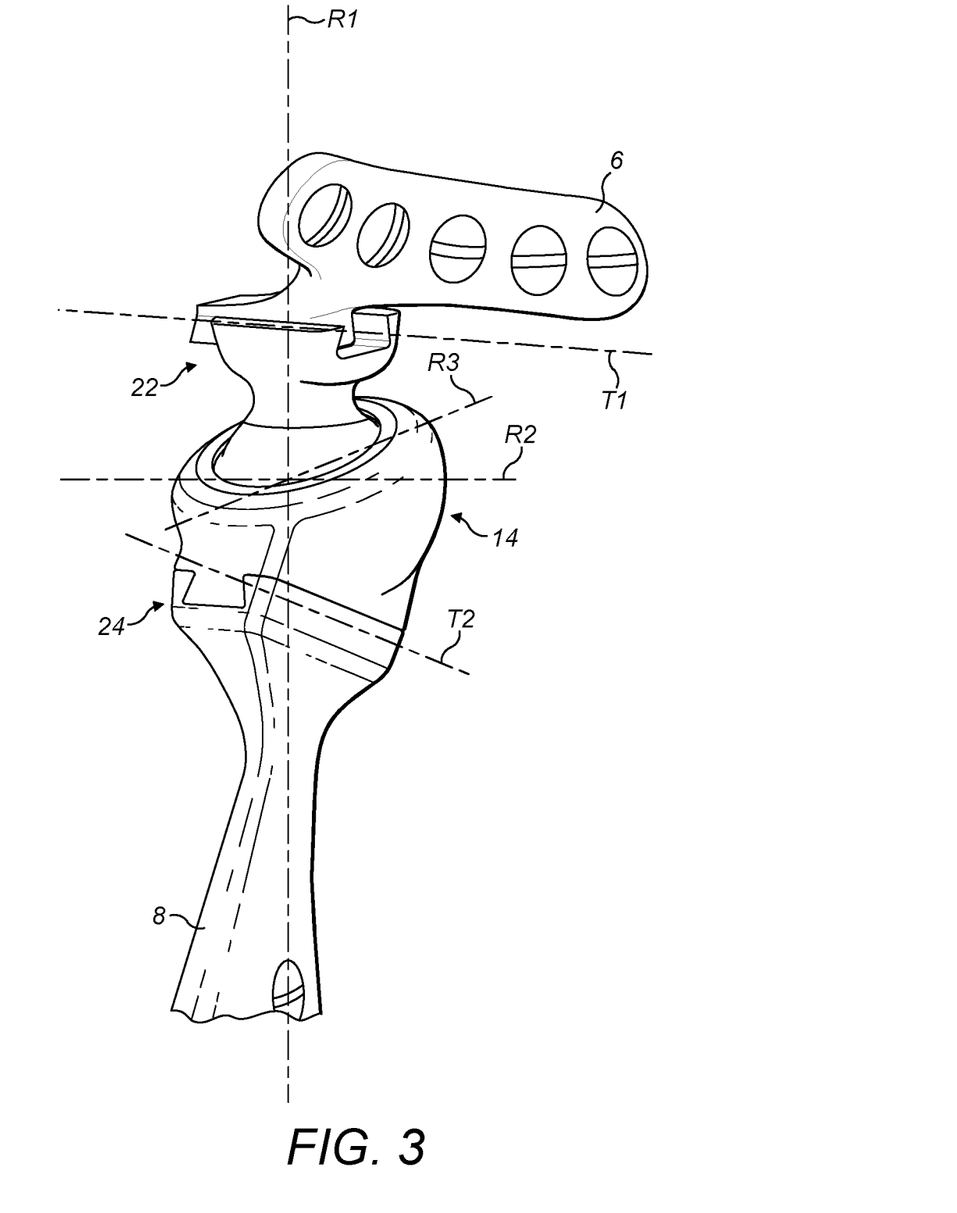
FIG. 3 shows axes for a range of motion of the embodiment.

Referring to FIG. 3, the range of motion of the mechanism 12 will be described for the present example. This range of motion determines the range of motion of the prosthesis when implanted.

The rotary joint in this example is rotatable about three orthogonal axes R1, R2, R3. A rotation of the rotary joint may be about one or a combination of any of these axes R1, R2, R3. Thus, a wide range of rotary motion is provided by the rotary joint.

As shown, the rotary joint 14 links the first slider joint 22 with the second slider joint 24. Thus, the configuration of the rotary joint determines a position of the first slider joint 22 with respect to a position of the second slider joint 24 when the prosthesis is not implanted.

The first translational range of motion given by the first slider joint is along a first translation axis T1. The second translational range of motion given by the second slider joint is along a second translation axis T2. The form of the first and second parts determines the orientation of the first and second translation axes T1, T2 respectively for the sliding joints for when the prosthesis is implanted. These orientations may be set when custom making the first and second parts 6, 8. Thus, for when the first part is attached to the temporal bone and the second part is attached to the mandible bone, the orientation of the first translation axis T1 relative to the second translation axis T2 is determined by the form of the first and second parts, and the configuration of the rotary joint about the rotary axes R1, R2 and R3 is determined by the orientation of the first and second translation axes.

In one example, the first and second parts are formed such that, when viewed along the first rotation axis R1, the first translation axis T1 and the second translation axis T2 are substantially perpendicular to each other when the prosthesis is implanted. Substantially perpendicular means that the first and second translation axes T1, T2 are oriented with respect to each other by an angle in the range of 80 to100 degrees, 85 to 95 degrees, 87 to 93 degrees, 89 to 91 degrees or by the angle 90 degrees. Thus, the combination of the first translational range of motion and the second translational range of motion determines a plane for translational motion of the first part 6 relative to the second part 8, and therefore, when the prosthesis is implanted, of the temporal bone relative to the mandible bone.

In an example, the substantially perpendicular relationship of the translation axes T1, T2 may be determined when custom making one or both of the first and second parts 6, 8. For example, the first part and the second part each have a surface for applying to the temporal or mandible bone, respectively; the orientation of these first and second surfaces relative to the first and second translation axes, respectively, may be set when making the first and second parts. Further, when implanting the prosthesis, a surface of the temporal or mandible bone to which the first or second part, respectively, is to be attached, may be shaped for example using a resection technique to determine the orientation of the translation axes relative to each other, described later.

In one example, the substantially perpendicular relationship of the translation axes T1, T2 is set for a patient when the temporal bone and the mandible bone are in an occluded state, in other words when the upper and lower jaws are closed. Moreover, when making the first and second parts 6, 8, the first and second translation axes T1, T2 may be set such that the orientation of the plane defined by the combination of the first and second translation axes lies substantially parallel to the plane of occlusion of the patient. The plane of occlusion is defined as the average plane where the teeth of the upper jaw meet the teeth of the lower jaw when the jaws are closed. Substantially parallel is defined herein to mean that the plane of the first and second translation axes T1, T2 is within +/−20 degrees, +/−17.5 degrees, +/−15 degrees, +/−7.5 degrees, +/−10 degrees, +/−7.5 degrees, +/−5 degrees, +/−2.5 degrees, +/−1 degree or 0 degrees with respect to the plane of occlusion. It has been found that orienting the first and second translation axes T1, T2 substantially perpendicular to each other, and such that the plane of translation is substantially parallel with the plane of occlusion, as described, provides one example where the temporo-mandibular joint prosthesis provides a good range of motion for a patient, when implanted. In other examples, it is envisaged that the orientation of the translation axes and of the plane of motion defined by the combined translation axes when the jaws are occluded may be different from the previously described example, to provide optimum functionality of the prosthesis whilst taking into account the specific anatomy of a patient.

In the examples described, the combination of the rotary range of motion and the first and second translational ranges of motion gives a wide range of overall motion for the temporo-mandibular joint prosthesis. This gives a greater range of motion for a patient implanted with the temporo-mandibular joint prosthesis compared with known prostheses. Moreover, with the greater range of motion, and the increased control of jaw movement which the mechanism gives to the patient over the range of motion, there is a reduced chance of one of the joints reaching a limit of its range of motion, which may lead to dislocation of that or another one of the joints of the mechanism. Moreover, the reduced chance of one of the joints reaching a limit of motion means it is less likely that undesired force is applied to the attachment of the first and second parts to the bones, for example to the osteosynthesis screws, thus reducing the risk of loosening of the attachment of the first and second parts to the bones.

In addition to the greater range of overall motion provided by the mechanism in the examples described, further measures contribute to the reduced risk of dislocation. For example, the use of dovetail slider joints for the first and second slider joints, as described previously, significantly restricts any separation of the protrusion and channel portions. This provides a suitably strong link between the first part and the rotary joint, and the second part and the rotary joint. Moreover, either of the first and second slider joints may be configured to limit an extent of the first and second translational range of motion, respectively, i.e. to provide a predetermined extent of translational motion, to prevent or reduce any risk of dislocation of the first and second slider joints. For example, a stop may be formed at each end of the slidable interface of either of the first and second slider joints, to limit the extent of translation. In some examples, the extent of the first translational range of motion and the second translational range of motion may be set for a specific patient; i.e. either of the first and second slider joints may be custom made for a patient. In other examples, an extent of the first and second translational ranges of motion may be set as standard for all patients. For example, an extent of the first translational range of motion in each direction along the first translation axis, starting from a closed position of the first slider joint, may be in the range of 20 to 5 millimeters, 17.5 to 5 millimeters, 15 to 5 millimeters, 12.5 to 7.5 millimeters, or 11 to 9 millimeters, or may be 10 millimeters. Further, for example, an extent of the second translational range of motion in each direction along the second translation axis, starting from a closed position of the second slider joint, may be in the range of 1 to 10 millimeters, 2.5 to 7.5 millimeters, or 4 to 6 millimeters, or 5 millimeters.

The rotary joint may also be configured to reduce or prevent dislocation of the first element from the second element. For example, the concave surface may be formed to surround the convex surface sufficiently such that a diameter of an opening of the second element through which the first element is received is less than a maximum diameter of the convex surface of the first element. In other embodiments, the diameter of the opening may be greater or the same as the maximum diameter of the convex surface, to allow the ball part to be fitted in the socket part during implantation of the prosthesis in a patient; in such a case, muscular tonus of the patient would provide support and stability to the rotary joint to prevent or reduce the chance of dislocation once the prosthesis has been implanted. Moreover, in some examples, the concave and convex surfaces may be shaped and sized to closely fit each other, to reduce or eliminate any non-rotary motion between the first and second elements of the rotary joint. Thus, the rotary joint may provide a suitably strong link between the first and second slider joints, and in turn the first and second parts. In examples, the rotary joint may be configured to provide a maximum range of rotational motion whilst also providing an acceptably low risk of dislocation. An extent of the rotational range of motion may be restricted by muscular tonus when the prosthesis has been implanted.

In an example, the first and second parts 6, 8 are formed of titanium or a titanium alloy such as titanium grade 2, and the first and second elements of the rotary joint are formed of zirconia, i.e. zirconium dioxide. It has been found that this combination of materials provides favorable properties for biocompatibility with the patient, and for reliable and effective operation of the mechanism and prosthesis as a whole, given the compact size of the mechanism. In another example, the first and second parts may instead be formed of zirconia. It is envisaged that in other examples different biocompatible materials may also provide favorable properties for the prosthesis. For example, any of the first part, the second part, the first element and the second element may be formed from cobalt-chromium, polyethylene, pyrolytic carbon, stainless steel, zirconia, titanium or titanium alloy.

Examples of operation of the example prosthesis described previously will now be given with reference to FIGS. 4 to 6.

Figure 4:
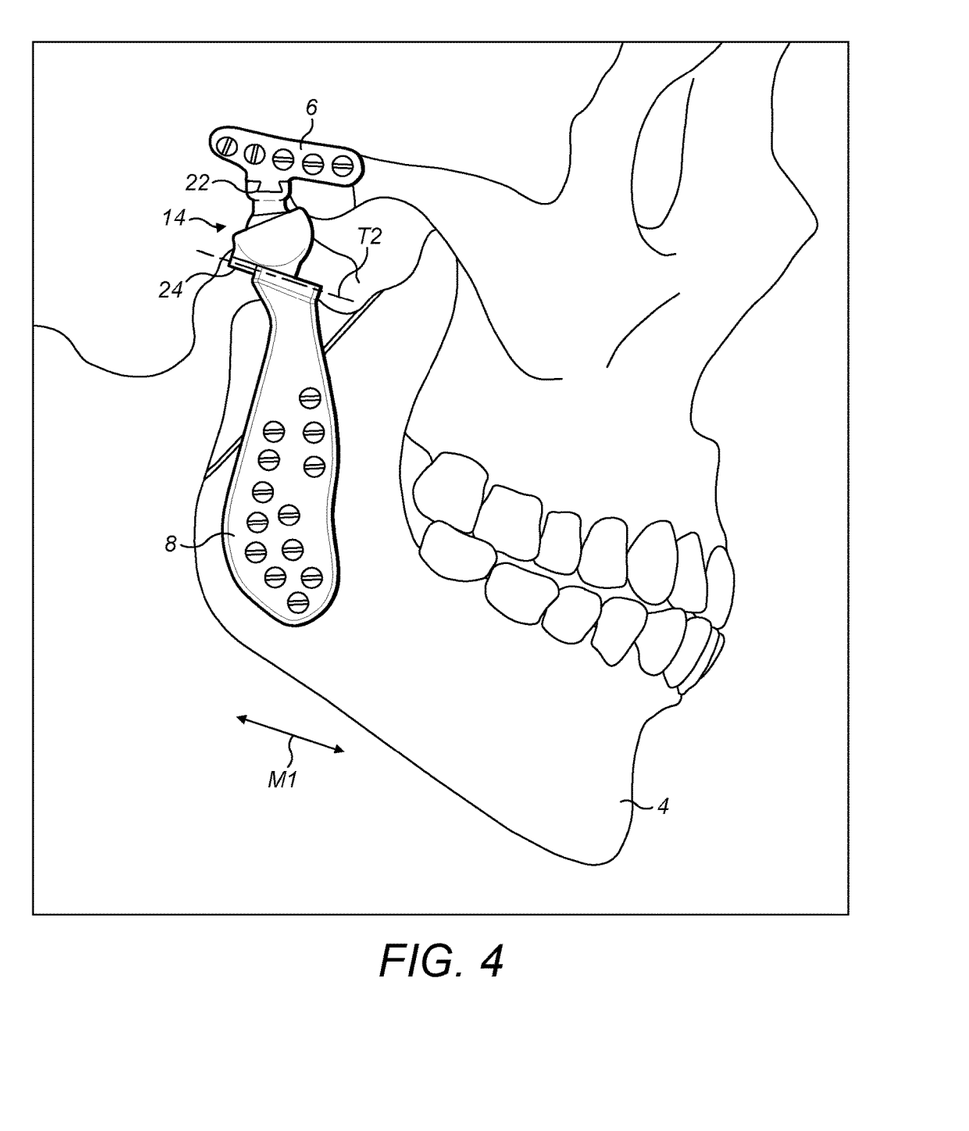
FIGS. 4, 5 and 6 show schematically examples of different movements of the prosthesis of the embodiment.

FIG. 4 shows an example translational movement M1 of the mandible bone 4, provided by sliding of the second slider joint 24 along the second translation axis T2, for protrusion or retrusion of the mandible bone 4.

Figure 5:
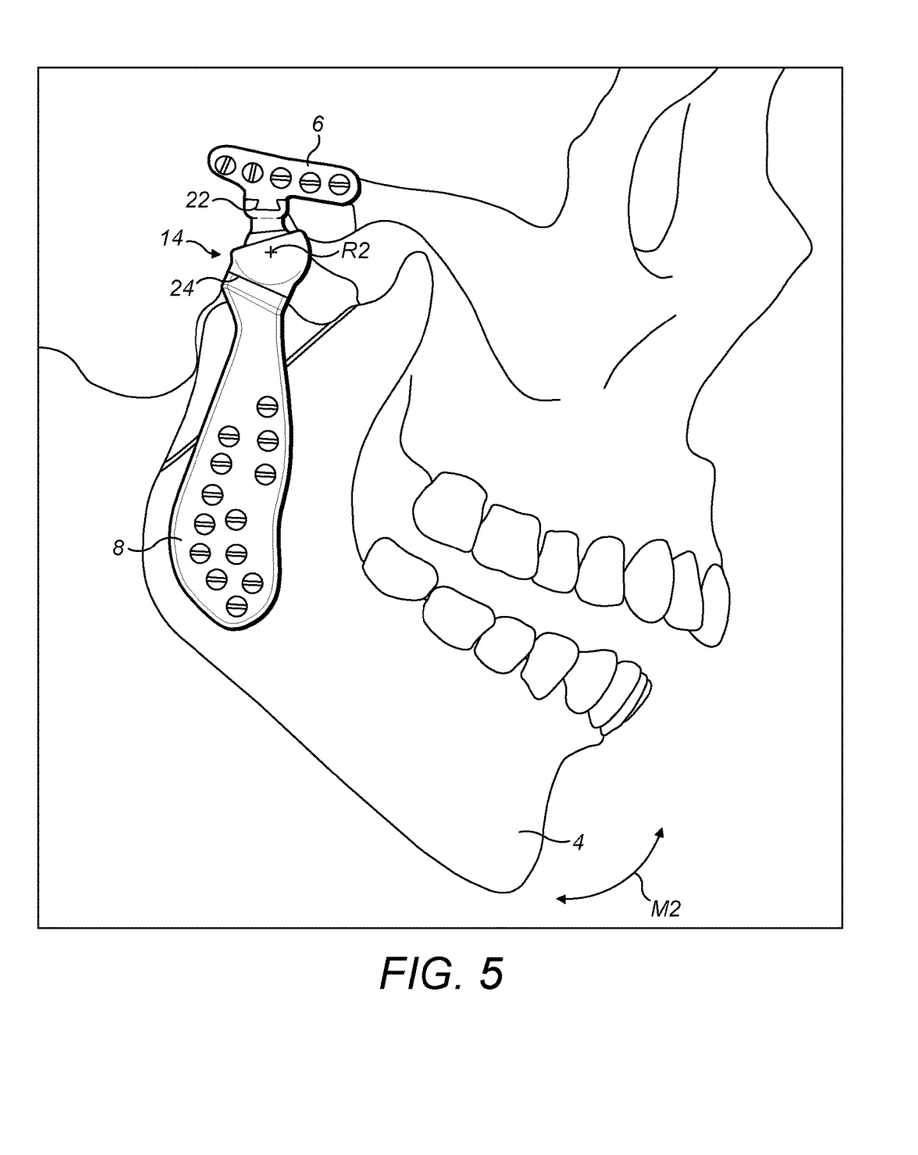

FIG. 5 shows an example rotational movement M2 of the mandible bone 4, provided by rotation of the second element relative to the first element in the rotary joint, about the second rotation axis R2, for opening and closing of the jaws.

Figure 6:
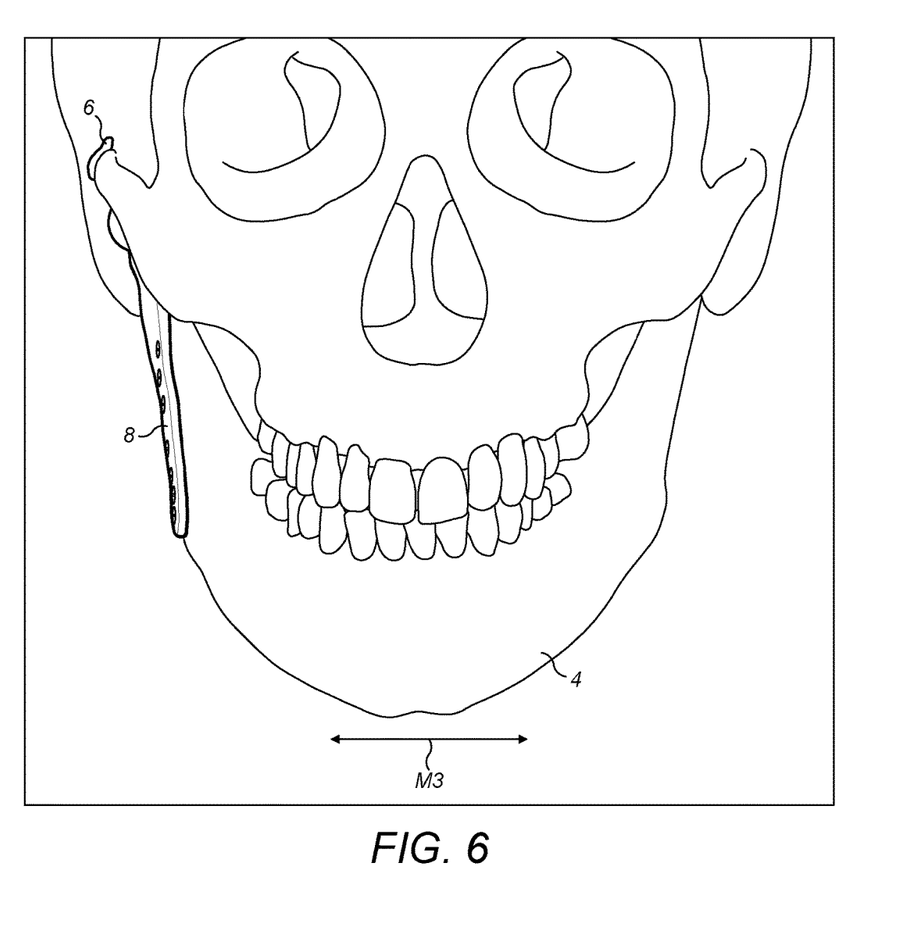

FIG. 6 shows an example translational movement M3 of the mandible bone 4, provided by sliding of the first slider joint (not shown in FIG. 6) along the first translation axis T1 (not shown in FIG. 6), for lateral movement of the mandible bone 4.

A temporo-mandibular joint prosthesis described herein may be implanted to replace one or both temporo-mandibular joints of a patient. This may be done for example in the case of a post-traumatic, degenerative, inflammatory or congenital pathology of the joint. Total reconstruction of the temporo-mandibular joint may quickly improve the life quality of a patient by increasing the mandibular opening and by reducing pain. The patient may be a human, but it is envisaged that the examples of temporo-mandibular joint prosthesis described herein may be used in animals.

Figure 7:
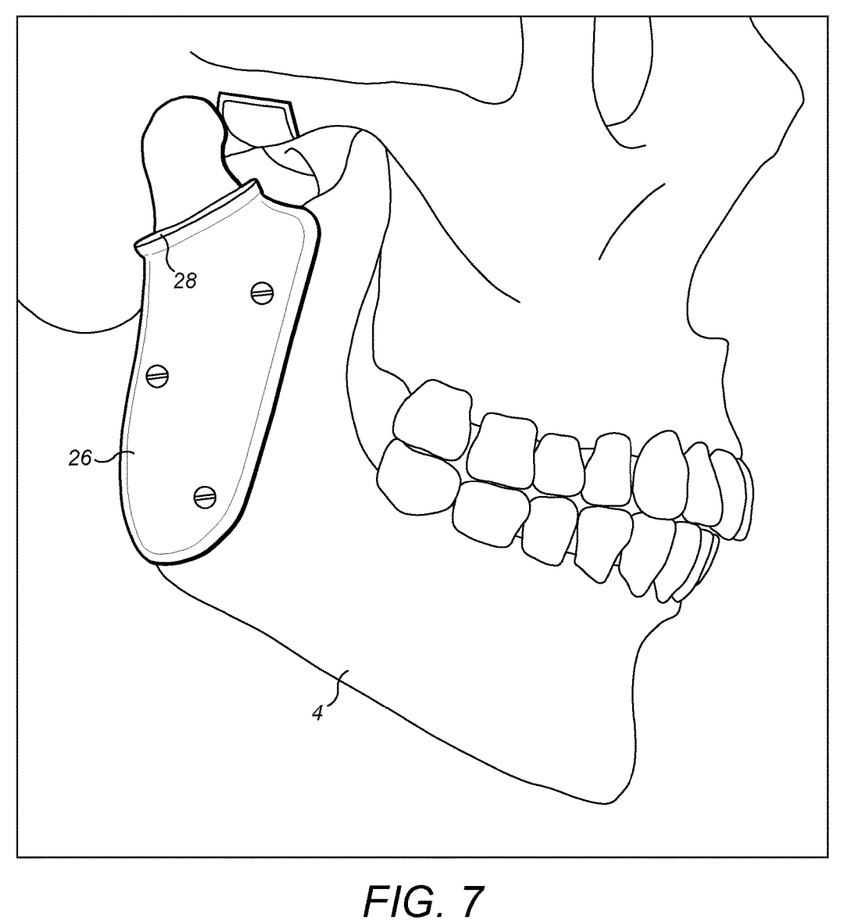
FIG. 7 shows schematically an example of a resection guide.

An overview of a method of implanting a temporo-mandibular joint prosthesis will now be described:

Total anaesthesia
Preauricular incision
Dissection to obtain temporo-mandibular joint exposition
Incision under the mandibular angle
Dissection to join temporo-mandibular joint exposition
Temporo-mandibular joint resection: two osteotomies, one for the temporal bone and one for the mandible bone
Patient jaws placed in occlusion
Insertion and osteosynthesis of first part of the prosthesis on zygomatic arch
Insertion of the second part of the prosthesis and prosthesis installation
Partial osteosynthesis of second part of the prosthesis
Functional control of the prosthesis, to determine desired positioning of prosthesis
Final osteosynthesis of the first and second parts of the prosthesis
Sutures In the resection step above, the form of the resection of either of the temporal and the mandible bones may be performed to determine the orientation of the first part relative to the second part, and therefore for example the orientation of the first translation axis relative to the second translation axis. A resection guide may be used for either of the temporal or mandible bones, for accurately cutting the bones, to ensure correct implantation of the prosthesis and orientation of the first and second parts relative to each other. FIG. 7 illustrates an example of a resection guide 26 attached to the mandible bone 4 for cutting the mandible bone accurately along a guide line 28 provided by the resection guide. The guide 26 may be attached to the bone with suitable screws, for example.

Whilst either or both of the first and second parts 6, 8 may be custom made for a patient, the rotary joint may be of a standard form for all patients. Therefore, one or both of the first and second parts 6, 8 may be manufactured and supplied separately from the rotary joint, for assembly for example by a surgeon.

In one example, the prosthesis is fully pre-assembled before implantation. In another example the first part and the first element may be pre-assembled together, via the first slider joint, and separately the second part and the second element may be pre-assembled together, via the second slider joint, without the rotary joint having yet been assembled; then, once the first part has been attached to the temporal bone and the second part attached to the mandible bone, the rotary joint may be assembled by connecting the first element and the second element together to rotatably interface with each other; a clip or clamp may be used to keep each of the slider joints in a closed position and from sliding whilst implanting the prosthesis; the clip or clamp may be removed after assembling the rotary joint.

The temporo-mandibular joint prosthesis described in examples herein provides a wide range of motion for the temporal bone relative to the mandible bone of a patient, thus more closely providing the range of motion of a natural temporo-mandibular joint compared with known prostheses, whilst also providing a reduced risk of dislocation. Indeed, the range of motion provided allows for circumduction, i.e. a circular type motion which occurs during for example mastication. The range of motion offered also reduces the risk of re-ankylosis, i.e. a stiffening of the prosthesis joints and/or the remaining natural temporo-mandibular joint where the prosthesis is fitted on only one side of a patient's jaws. Further, the temporo-mandibular joint prosthesis described herein is sufficiently compact to fit within the limited space between the temporal bone and mandible bone, without interfering with other parts of the skull and without protruding externally from the skull, which might disfigure a side of a patient's head.

Examples described above have a mechanism with a rotary joint and two slider joints. It is envisaged that the mechanism may include a different number of joints. For example, the mechanism in a further example may include a rotary joint and one slider joint with a translation axis for example either for lateral or for protrusion/retrusion of the mandible. Such a mechanism would still provide a greater range of motion than known prostheses and may allow a more compact mechanism to be provided, for example where the space for accommodating the prosthesis in a patient is more limited.

The above embodiments are to be understood as illustrative examples. Further embodiments of the invention are envisaged. For example, regarding the types of joints described previously, it is envisaged that an alternative form of slider joint may be used instead of the dovetail slider joint described previously. Such alternative slider joints may be configured to reduce or prevent dislocation of the joint, and to determine a desired extent of translation. Further, although the rotary joint is described above with the first element providing the ball and the second element providing the socket of the ball and socket joint, which contributes to a compact design of the prosthesis, in other examples the first element may provide the socket and the second element may provide the ball. In other examples, a different type of rotary joint may be used than a ball and socket joint.

Figure 8:
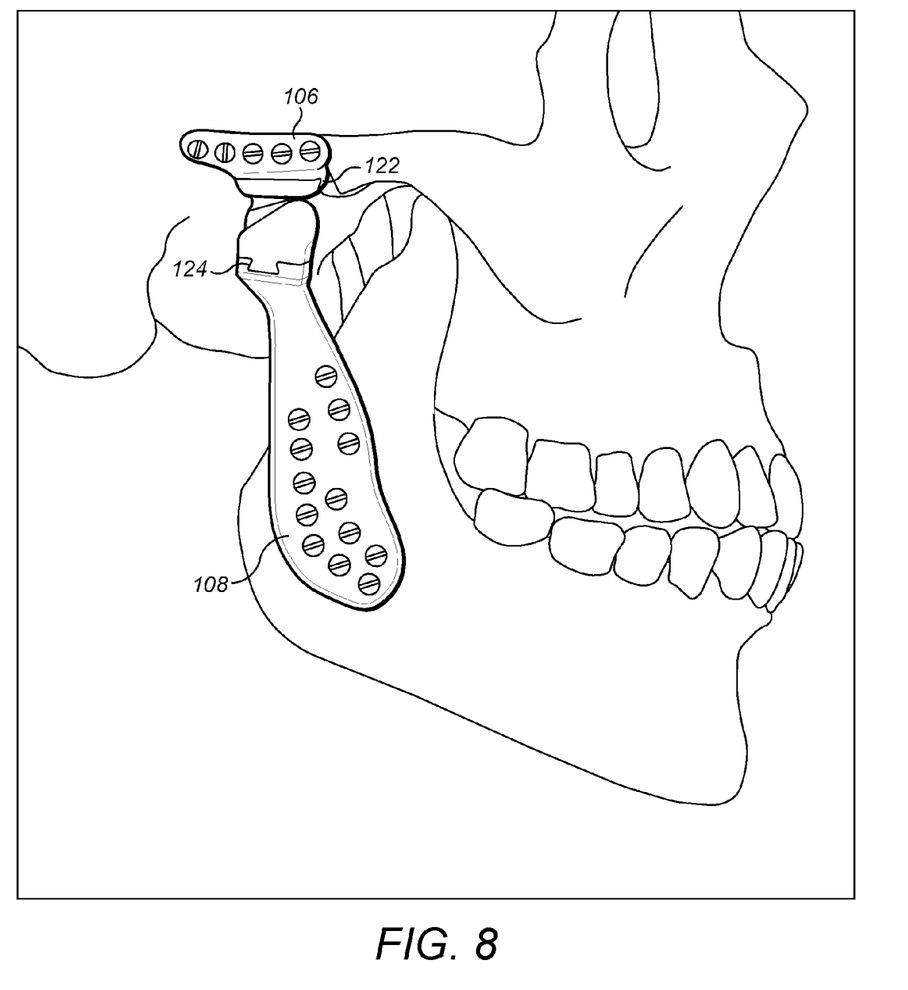
FIG. 8 shows schematically a different embodiment of a temporo-mandibular joint prosthesis.

As illustrated in FIG. 4, the second slider joint may be oriented to provide protrusion and retrusion of the lower jaw, with an example translational movement M1, and the first slider joint may be oriented substantially perpendicularly to the second slider joint, to provide a lateral movement as illustrated in FIG. 6 with example translational movement M3. In an alternative example, the first and second slider joints may be oriented differently, as illustrated in FIG. 8. In FIG. 8, features similar to those described previously are labelled with the same reference numerals, incremented by 100; corresponding descriptions should be taken to apply unless explained otherwise. In this example, the first slider joint 122 is instead oriented to provide the translational movement for protrusion and retrusion. The second slider joint 124 in this example is oriented such that the second translation axis of the second slider joint is substantially perpendicular to the first translation axis of the first slider joint; thus the second slider joint 124 provides lateral movement of the lower jaw.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the accompanying claims.

What is claimed is:

1. A temporo-mandibular joint prosthesis comprising:
a first part for attaching to a temporal bone;
a second part for attaching to a mandible bone; and
a mechanism linking the first part and the second part, the mechanism defining a range of motion of the first part relative to the second part for when the first and second parts are attached to the temporal bone and the mandible bone, respectively, the mechanism including:
a rotary joint providing a rotational range of motion of the first part relative to the second part;
a first slider joint providing a first translational range of motion of the first part relative to the second part; and
a second slider joint providing a second translational range of motion of the first part relative to the second part,
the rotary joint comprising a first element and a second element, a surface of the first element rotatably interfacing with a surface of the second element, wherein the first part is linked to the first element by the first slider joint.

2. A temporo-mandibular joint prosthesis according to claim 1, wherein the second part is linked to the second element by the second slider joint.

3. A temporo-mandibular joint prosthesis according to claim 1, the first translational range of motion being along a first translation axis and the second translational range of motion being along a second translation axis, wherein the first and second parts are formed to determine that an orientation of the first translation axis is substantially perpendicular to an orientation of the second translation axis when the first and second parts are attached to the temporal bone and the mandible bone, respectively.

4. A temporo-mandibular joint prosthesis according to claim 1, wherein the second slider joint is configured to provide a predetermined extent of the second translational range of motion.

5. A temporo-mandibular joint prosthesis according to claim 1, wherein the first slider joint is configured to provide a predetermined extent of the first translational range of motion.

6. A temporo-mandibular joint prosthesis according to claim 1, wherein the rotary joint is formed of zirconia and at least one of the first part and the second part are formed of titanium or a titanium alloy.

7. A temporo-mandibular joint prosthesis according to claim 1, wherein the rotary joint comprises a ball and socket joint.

8. A temporo-mandibular joint prosthesis according to claim 1, wherein at least one of the first and second slider joints comprises a dovetail slider joint.

9. A temporo-mandibular joint prosthesis comprising:
a first part for attaching to a temporal bone;
a second part for attaching to a mandible bone; and
a mechanism linking the first part and the second part, the mechanism defining a range of motion of the first part relative to the second part for when the first and second parts are attached to the temporal bone and the mandible bone, respectively, the mechanism including:
a rotary joint providing a rotational range of motion of the first part relative to the second part;
a first slider joint providing a first translational range of motion of the first part relative to the second part; and
a second slider joint providing a second translational range of motion of the first part relative to the second part,
wherein the first slider joint is linked to the second slider joint by the rotary joint.

10. A temporo-mandibular joint prosthesis according to claim 9, wherein the second slider joint is configured to provide a predetermined extent of the second translational range of motion.

11. A temporo-mandibular joint prosthesis according to claim 9, wherein the first slider joint is configured to provide a predetermined extent of the first translational range of motion.

12. A temporo-mandibular joint prosthesis according to claim 9, wherein the rotary joint is formed of zirconia and at least one of the first part and the second part are formed of titanium or a titanium alloy.

13. A temporo-mandibular joint prosthesis according to claim 9, wherein at least one of the first and second slider joints comprises a dovetail slider joint.

14. A temporo-mandibular joint prosthesis according to claim 9, the first translational range of motion being along a first translation axis and the second translational range of motion being along a second translation axis, wherein the first and second parts are formed to determine that an orientation of the first translation axis is substantially perpendicular to an orientation of the second translation axis when the first and second parts are attached to the temporal bone and the mandible bone, respectively.

15. A temporo-mandibular joint prosthesis according to claim 9, wherein the rotary joint comprises a ball and socket joint.

\* \* \* \* \*